United States Patent [19]

Hammond et al.

[11] Patent Number: 4,868,286
[45] Date of Patent: Sep. 19, 1989

[54] TRANSLATION INHIBITING PEPTIDE

[75] Inventors: Graeme L. Hammond, North Haven; Pamela A. Havre, New Haven, both of Conn.

[73] Assignee: Yale University, New Haven, Conn.

[21] Appl. No.: 81,929

[22] Filed: Aug. 5, 1987

[51] Int. Cl.[4] .................. C07K 15/00; C07K 7/08; C07K 7/10

[52] U.S. Cl. .................. 530/350; 530/300; 530/324; 530/325; 530/326

[58] Field of Search .................. 530/300, 324–326, 530/350

[56] References Cited

PUBLICATIONS

R. Z. Litten, B. J. Martin, R. B. Low and N. R. Alpert, "Altered Myosin Isozyme Patterns from Pressure-Overloaded and Thyrotoxic Hypertrophied Rabbit Hearts", Cir. Res., 50, 856–863, (1982).

G. L. Hammond, B. Nadal-Ginard, N. S. Talner and C. L. Market, "Myocardial LDH Isozyme Distribution in the Ischemic and Hypoxic Heart", Circulation, 53, 637–643, (1976).

J. S. Ingwall, M. F. Kramer, M. A. Fifer, B. H. Lorell, R. Shemin, W. Grossman and P. D. Allen, "The Creatine Kinase System in Normal and Diseased Human Myocardium", N. Engl. J. Med., 313, 1050–1054, (1985).

T. Wisenbaugh, P. Allen, G. Cooper, H. Holzgrefe, G. Beller and B. Carabello, "Contractile Function, Myosin ATPase Activity and Isozymes in the Hypertrophied Pig Left Ventricle after a Progressive Pressure Overload", Circ. Res., 53.

J-J. Mercadier, P. Bouveret, L. Gorza, S. Schiaffino, W. A. Clark, R. Zak, B. Swynghedauw and K. Schwartz, "Myosin Isoenzymes in Normal and Hypertrophied Human Ventricular Myocardium", Circ. Res., 53, 52–62, (1983).

N. R. Alpert and L. A. Mulieri, "Increased Myothermal Economy of Isometric Force Generation in Compensated Cardiac Hypertrophy Induced by Pulmonary Artery Constriction in the Rabbit", Cir. Res., 40, 491–500, (1982).

Y. K. Lai, P. A. Havre and G. L. Hammond, "Cardiac Hypertrophy Cannot Proceed Without Initial Suppression of Protein Synthesis", Biochem. Biophys. Res. Comm., 135, 857–863, (1986).

Y-K. Lai, P. A. Havre and G. L. Hammond, "Heat Shock Stress Initiates Simultaneous Transcriptional and Translational Changes in the Dog Heart", Biochem. Biophys. Res. Comm., 134, 166–171, (1986).

G. L. Hammond, Y-K. Lai and C. L. Markert, "Diverse Forms of Stress Lead to New Patterns of Gene Expression Through a Common and Essential Metabolic Pathway", Proc. Natl. Acad. Sci., 79, 3485–3488, (1982).

G. L. Hammond, Y-K. Lai and C. L. Markert, "Preliminary Characterization of Molecules that Increase Cell Free Translational Activity of Cardiac Cytoplasmic RNA", Symposium on Biology of Cardiac Overload. Eur. Heart J., 5(Supp), 225–229, (1984).

E. A. Breisch, F. C. White and B. M. Bloor, "Myocardial Characteristics of Pressure-Overload Hypertrophy. A Structural and Functional Study", Lab. Invest., 51, 333–342, (1984).

P. Y. Hatt, K. Rakusan, P. Gastineau and M. Laplace, "Morphometry and Ultra-Structure of Heart Hypertrophy Induced by Chronic Volume Overload (Aorta-Caval Fistula in the Rat)", J. Mol. Cell. Cardiol., 11, 989–998, (1979).

(List continued on next page.)

Primary Examiner—Delbert R. Phillips
Assistant Examiner—Abdel A. Mohamed
Attorney, Agent, or Firm—Spring Horn Kramer & Woods

[57] ABSTRACT

A peptide that causes a suppression in protein synthesis by halting the translation of mRNA into protein, the peptide having a Stokes radius of less than 16 Angstroms, a molecular weight, determined by SDS-PAGE, of 17 kD (indicating that the peptide is a monomer) and an isoelectric point of 7.25. The peptide of the present invention may have therapeutic advantages in halting the proliferation of abnormal or excess protein, such as in malignancies, IHSS or hemi-hypertrophy.

11 Claims, 7 Drawing Sheets

OTHER PUBLICATIONS

P. Anversa, C. Beghi, V. Levicky, S. L. McDonald and Y. Kikkawa, "Morphometry of Right Ventricular Hypertrophy Induced by Strenous Exercise in Rat", *Am. J. Physiol.*, 243, H856–H861, (1982).

F. Z. Meerson, "Development of Modern Components of the Mechanism of Cardiac Hypertrophy", *Cir. Res., Suppl II,* 35, 58, (1987).

L. P. McCallaster and E. Page, "Effects of Thyroxin on Ultrastructure of Rat Myocardial Cells: A Stereological Study", *J. Ultrastr. Res.*, 42, 136–155, (1973).

TRANSLATION INHIBITING PEPTIDE

GOVERNMENT RIGHTS

This invention was made with United States Government support under Grant HL 24511-06 from the NIH. The United States Government has certain rights in this invention.

BACKGROUND OF THE INVENTION

1. Field of the Invention

The present invention concerns a peptide that causes a marked suppression in protein synthesis. More particularly, the present invention concerns a translation inhibiting peptide obtained from canine cardiac tissue.

2. Background Information

A fundamental question concerning initiation of cardiac hypertrophy is: how can energy be diverted to start the process when the heart itself must function more vigorously? In established hypertrophy, many adaptive factors such as reduced ATPase activity (R. Z. Litten, B. J. Martin, R. B. Low and N. R. Alpert, "Altered Myosin Isozyme Patterns form Pressure-overloaded and Thyrotoxic Hypertrophied Rabbit Hearts", Cir. Res., 50, 856-863, (1982)) and shifts in LDH (G. L. Hammond, B. Nadal-Ginard, N. S. Talner and C. L. Market, "Myocardial LDH Isozyme Distribution in the Ischemic and Hypoxic Heart", Circulation, 53, 637-643, (1976)), CPK (J. S. Ingwall, M. F. Kramer, M. A. Fifer, B. H. Lorell, R. Shemin W. Grossman and P. D. Allen, "The Creatine Kinase System in Normal and Diseased Human Myocardium", N. Engl. J. Med., 313, 1050-1054, (1985)) and possibly myosin isozyme patterns (T. Wisenbaugh, P. Allen, G. Cooper, H. Holzgrefe, G. Beller and B. Carabello, "Contractile Function, Myosin ATPase Activity and Isozymes in the Hypertrophied Pig Left Ventricle after a Progressive Pressure Overload", Circ. Resl, 53, 52-62, (1983); J-J. Mercadier, P. Bouveret, L. Gorza, S. Schiaffino, W. A. Clark, R. Zak, B. Swynghedauw and K. Schwartz, "Myosin Isoenzymes in Normal and Hypertrophied Human Ventricular Myocardium", Circ. Res., 53, 52-62, (1983)) permit anaerobic energy delivery and increased economy of isometric force development (N. R. Alpert and L. A. Mulieri, "Increased Myothermal Economy of Isometric Force Generation in Compensated Cardiac Hypertrophy Induced by Pulmonary Artery Constriction in the Rabbit", Cir. Res., 40, 491-500, (1982)) so that the heart can function more efficiently given the constraints imposed by the chronic stress. In acute cardiac stress, however, such as that produced by sudden aortic banding, the heart still must generate increased contractile force during the time necessary for adaptation, but in the absence of these adaptive measures.

In order to meet the dual requirements of increased contractile force and the initiation of hypertrophy, the acutely stressed cardiac cell saves energy by temporarily throttling down or turning off other non-imminently essential cell functions. Although the end result of hypertrophy is increased protein synthesis, it has been previously reported that one of the earliest responses of cardiac cells to acute stress, imposed either by heat shock or aortic banding, was suppression of protein synthesis caused, at least in part, by translational inhibition, (Y. K. Lai, P. A. Havre and G. L. Hammond, "Cardiac Hypertrophy Cannot Proceed Without Initial Suppression of Protein Synthesis", Biochem. Biophys. Res. Comm., 135, 857-863, (1986)).

Heretofore it has been noted that the aforementioned suppression was associated with a shift in the polysome profile towards the monosome region, (Y-K. Lai, P. A. Havre and G. L. Hammond, "Heat Shock Stress Initiates Simultaneous Transcriptional and Translational Changes in the Dog Heart", Biochem. Biophys. Res. Comm., 134, 166-171, (1986)). As has been previously shown, both stresses share in common a discrepancy between energy requirements and expenditure resulting in similar immediate changes in cell biochemistry, (G. L. Hammond, Y-K. Lai and C. L. Markert, "Diverse Forms of Stress Lead to New Patterns of Gene Expression Through a Common and Essential Metabolic Pathway", Proc. Natl. Acad. Sci., 79, 3485-3488, (1982)).

G. L. Hammond, Y-K. Lai and C. L. Markert, "Preliminary Characterization of Molecules that Increase Cell Free Translational Activity of Cardiac Cytoplasmic RNA", Symposium on Biology of Cardiac Overload. Eur. Heart J., 5(Supp), 225-229, (1984) prepared extracts from normal and experimental canine hearts in which a 100 mm Hg gradient was created across the ascending aorta for 6 hours. Experimental extracts were then treated (1) by ultrafiltration through YM 10 and YM 30 membranes, (2) by incubation with immobilized trypsin for 1 hour at 37° C. and (3) by incubation in a boiling water bath for 10 minutes. Extracts were perfused through isolated rat hearts for 1 hour. Total cytoplasmic RNA was then extracted from the perfused heart and translated in a cell free medium containing [$^{35}$S]-methionine Incorporated label into newly synthesized protein was determined by liquid scintillation counting. A 13% mean increase in translational activity was produced by the fraction of the experimental extract passing through the YM 10 membrane compared with the material retained by YM 10 and YM 30 membranes. A 14% mean decrease in translational activity was observed in hearts perfused with experimental extracts treated with immobilized trypsin compared to untreated experimental extracts. There was no reported significant difference in translational activity of hearts perfused with experimental extracts subjected to boiling compared with non-boiled experimental extracts. The above data were said to suggest that the active molecules may be heat stable peptides or peptide containing substances of 10,000 daltons or less in molecular weight.

Hypertrophy represents the final visible result of a sequence of complex and precisely programmed events that are extremely difficult to unravel. To complicate the issue, the cardiac hypertrophy associated with pressure overload, (E. A. Breisch, F. C. White and B. M. Bloor, "Myocardial Characteristics of Pressure-overload Hypertrophy. A Structural and Functional Study", Lab. Invest., 51, 333-342, (1984)), volume overload, (P. Y. Hatt, K. Rakusan, P. Gastineau and M. Laplace, "Morphometry and Ultrastructure of Heart Hypertrophy Induced by Chronic Volume Overload (Aorta-caval Fistula in the Rat)", J. Mol. Cell. Cardiol., 11, 989-998, (1979)), exercise training, (P. Anversa, C. Beghi, V. Levicky, S. L. McDonald and Y. Kikkawa, "Morphometry of Right Ventricular Hypertrophy Induced by Strenous Exercise in Rat", Am. J. Physiol., 243, H856-H861, (1982)), ischemia, (F. Z. Meerson, "Development of Modern Components of the Mechanism of Cardiac Hypertrophy", Cir. Res., Suppl II, 35, 58, (1987)), and thyroxin administration (L. P. McCallaster and E. Page, "Effects of Thyroxin on Ultrastructure of Rat Myocardial Cells: A Stereological Study", *J. Ultrastr. Res.*, 42, 136-155, (1973)), are all slightly different, raising the possibility that there may be many molecular inducers of hypertrophy.

| DEFINITIONS | |
|---|---|
| Asp | aspartic acid |
| Asn | asparagine |
| Asx | aspartic acid and/or asparagine |
| Glu | glutamic acid |
| Glx | glutamic acid and/or glutamine |
| Ser | serine |
| Gly | glycine |
| Gln | glutamine |
| His | histidine |
| Arg | arginine |
| Thr | threonine |
| Ala | alanine |
| Pro | proline |
| Tyr | tyrosine |
| Val | valine |
| Met | methionine |
| Ile | isoleucine |
| Leu | leucine |
| Phe | phenylalanine |
| Lys | lysine |

SUMMARY OF THE INVENTION

The present invention concerns a protein that causes a marked suppression in protein synthesis. The protein, hereinafter referred to as "translation inhibiting peptide" or "TIP", can be isolated from the organs, tissues and muscles of mammmals, e.g., cardiac tissue, e.g., canine cardiac tissue.

TIP has a molecular weight, determined by SDS-PAGE, of 12 to 17 KD, preferably 17 KD. TIP has an isoelectric point of 7 to 7.25, preferably 7.25 and a high content of Asx (aspartic acid (Asp) and asparagine (Asn)), Glx (glutamic acid (Glu) and glutamine (Gln)). Furthermore, TIP has a Stokes radius of less than 16 Å, preferably 10 to 15 Å.

TIP halts translation of mRNA into protein.

TIP is heat stable and water soluble.

DETAILED DESCRIPTION OF THE INVENTION

Figure 1:
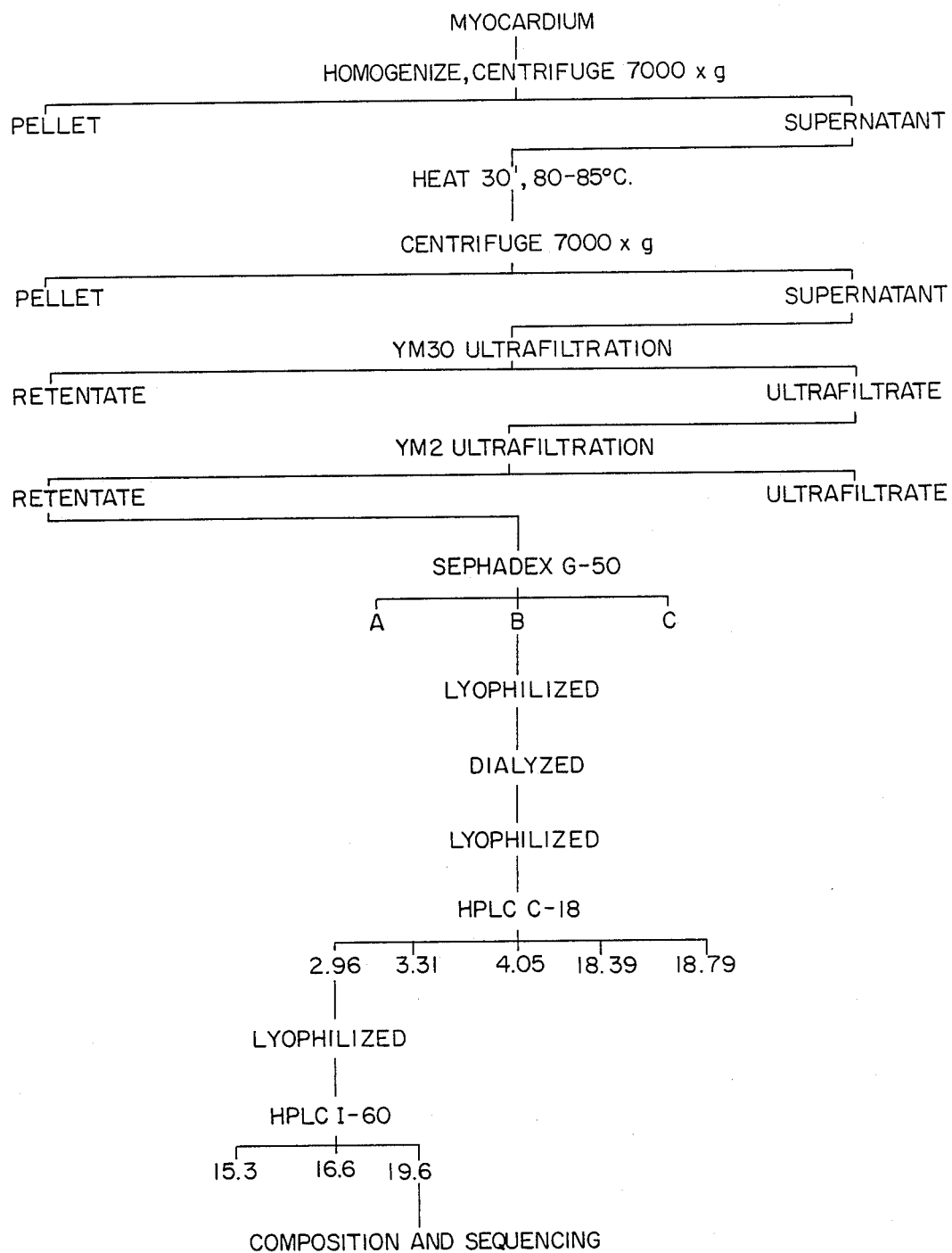
FIG. 1 is a schematic diagram for a purification scheme of cardiac tissue for the isolation of translation inhibiting peptide.

TIP may be isolated from the tissues, organs, e.g., heart, lung, liver, kidney, stomach, intestines and muscles of a mammal, e.g., a human or a dog.

Without wishing to be bound by any particularly theory of operability, TIP may act by obstructing one or more of the following steps involved in the initiation of protein synthesis: (1) methionine binding to the initiator tRNA, (2) binding of methionyl tRNA to the 40S ribosomal subunit, (3) catalysis by initiation factors, (4) binding of the initiator tRNA to a specific start codon on the mRNA and (5) dissociation of the initiation factor from the 40S subunit to allow binding of the 60S subunit. A substance that interfered with any one of these initiation steps would decrease the number of ribosomes bound to mRNA causing a shift from polysomes toward monosomes.

In non-mammalian species, heat shock activates a mechanism that discriminates against normal mRNAs as a class, but allows heat shock mRNAs to be translated with very high efficiency, (S. Lindquist, "Translational Efficiency of Heat-induced Messages in Drosophila Melanogaster Cells", *J. Mol. Biol.*, 137, 151-158, (1980)).

Conceivably, activation of TIP, which occurs in response to heat shock or aortic banding, may cause binding to the initiator region of normal mRNAs, blocking the ribosome binding site, and thereby decreasing the number of ribosomes per message. It is believed that the mRNAs for stress proteins would have a slightly different initiator region so that TIP would not compete with ribosomes for this site, allowing synthesis of stress proteins to continue in the absence of normal protein synthesis.

Alternatively TIP may be a RNase or a phosphatase, but TIP is significantly distinct from ribonuclease, since ribonuclease has an isoelectric point of 9 and an amino acid composition very different than TIP. For example, bovine ribonuclease has about 50% as much Asx as contained in TIP, one-third as much Glx, 10% as much Gly, about twice as much Thr, Lys, Val, Met and Leu and about three times as much Tyr.

In the first case, TIP would cleave the RNA regions between ribosomes to generate shorted mRNA fragments bearing fewer ribosomes. However, this seems unlikely as the amount of translatable mRNA increases with acute cardiac stress, (Hammond, Wilson and Markert, supra; G. L. Hammond, Y-K. Lai and C. L. Markert, "The Molecules that Initiate Cardiac Hypertrophy are Not Species-specific", *Science*, 216, 529-531, (1982)) and, in non-mammalian species, the translation efficiency of mRNA decreases with heat shock, but the mRNAs themselves are not destroyed (Linquist, supra). If TIP was a phosphatase, it might dephosphorylate S6, a component of the 40S subunit. The recruitment of MRNA into polysomes is found to be correlated with the state of S6 phosphorylation in HeLa cells, (P. J. Nielsen, R. Duncan and E. H. McConkey, "Phosphorylation of Ribosomal Protein S6", *Eur. J. Biochem.*, 120, 523-527, (1981)). When S6 is dephosphorylated, it has a lower affinity for mRNA. Therefore it is believed that dephosphorylation would also cause a shift in the direction of polysomes toward monosomes. Heat shock of HeLa cell suspension cultures has been shown to cause a rapid, but reversible decline in the phosphorylation level of S6, (A. S. Olsen, D. F. Triemer and M. M.

Sanders, "Dephosphorylation of S6 and Expression of the Heat Shock Response in Drosophila Melanogaster", *Mol. Cell Biol.*, 3, 2017-2027, (1983); M. M. Sanders. D. Feeney-Triemer, A. S. Olsen and J. Farrell-Towt, in *Heat Shock: From Bacteria to Man*, (M. J. Schlesinger, M. Ashburner and A. Tissieres, Eds), Cold Spring Harbor, N.Y.: Cold Spring Harbor Laboratory, (1982) pp. 234-242).

The mechanism by which TIP causes translational inhibition is unknown, but increased TIP activity appears to be an essential first step, probably related to saving cellular energy, as the cell redirects its resources in an effort to remain viable while preparing for the subsequent development of hypertrophy.

It is believed that TIP may have therapeutic advantages in such cases where abnormal or excess proteins are synthesized, such as in malignancies, IHSS hemihypertrophy, keloid formation, gum hyperplasia and hypertrophic scar.

It was found that treatment of polysome preparations, obtained from control canine hearts, with purified TIP sharply shifted the polysome distribution profile to one in which monosomes predominated. It was found that 2.4 ng of TIP completely inhibited the translation of 1 μg of RNA.

It is believed that translational inhibition is an essential initial reaction to acute stress that allows the cell to redirect energy into vital cell functions, while preparing for hypertrophy.

The invention will now be described with reference to the following non-limiting examples.

EXAMPLES

EXAMPLE 1: Stress Induction

Eighteen adult mongrel dogs were anesthetized with sodium pentabarbitol (25 mg/kg) and their chests were opened through a median sternotomy. Six hearts, used for controls, were acutely excised. The six hearts were stressed for one hour by ascending aortic banding to a 40-50 mm Hg gradient and the six hearts were stressed by in vivo heat shock to 42° C. for one hour as described in Lai, Havre and Hammond, *Biochem. Biophys. Res. Comm.*, 134, 166-171, (1986). Upon completion of the stress, the hearts were excised and the ventricular myocardium was used for protein extraction and purification.

EXAMPLE 2: Peptide Purification

Figure 2:
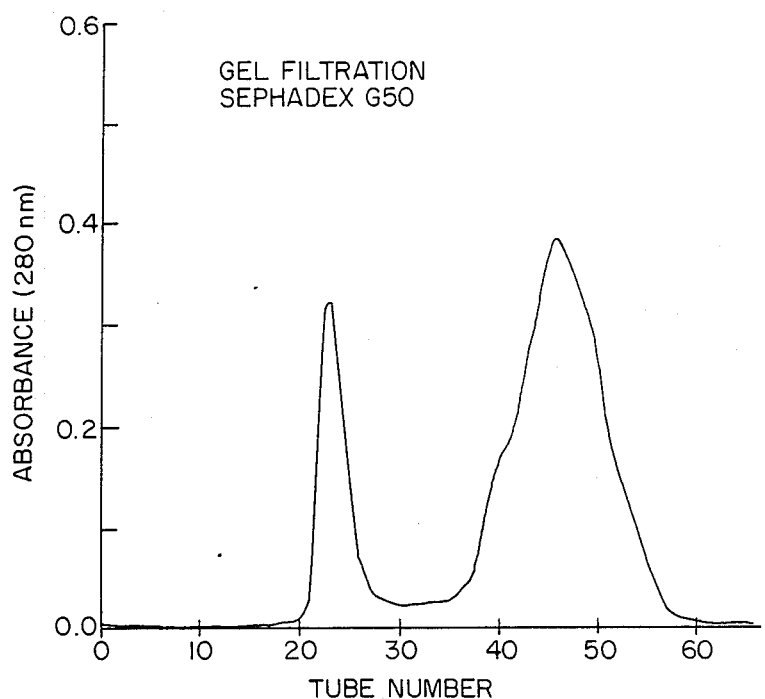
FIG. 2 is a graph depicting the results of a "SEPHADEX G-50" chromatograph.
Figure 3:
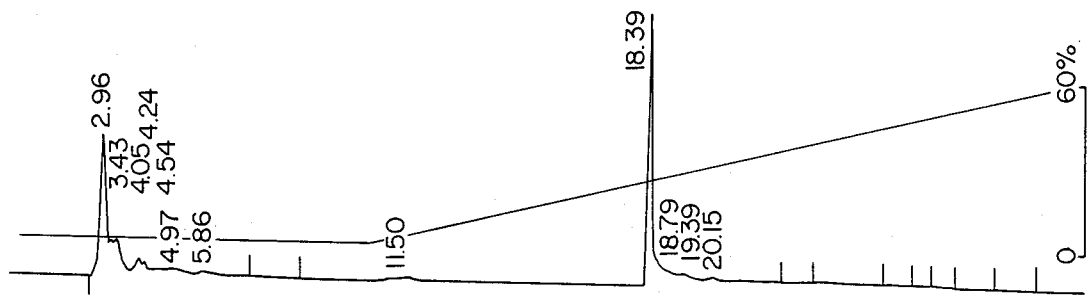
FIG. 3 is the results of a reverse phase HPLC.
Figure 4:
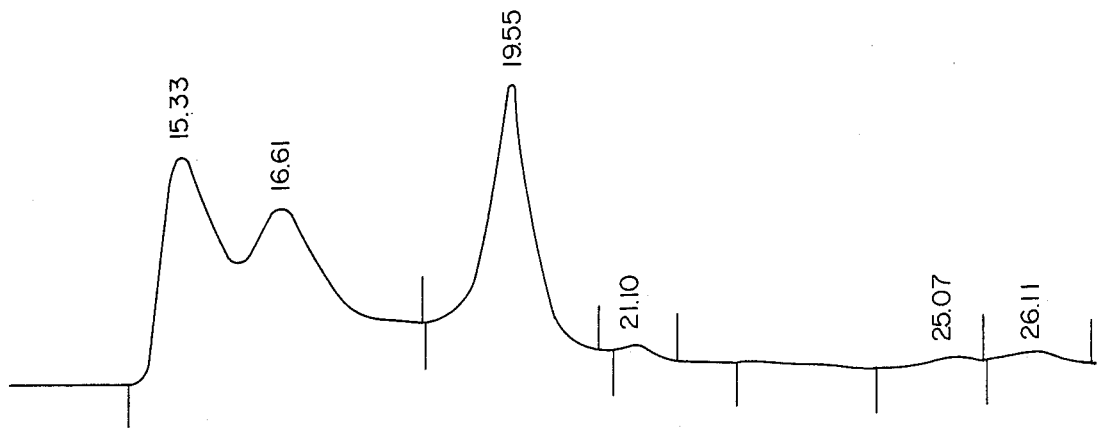
FIG. 4 is a plot depicting the results of a HPLC gel filtration.

Proteins obtained from Example 1 were purified by the following scheme:

The purification scheme, outlined in FIG. 1 began with 200 g of left ventricle as starting material. The tissue was homogenized in 800 ml dionized distilled water using a Brinkman polytron fitted with a PT 35/4 probe for one minute at the highest power setting. The homogenate was centrifuged for 30 minutes at $7000 \times g$ at 4° C. and the supernatant was heated for 30 minutes at 80°-85° C. and centrifuged again using the same conditions. The supernatant was passed through a YM 30 membrane and the ultrafiltrate concentrated to a final volume of 15 ml using a YM 2 membrane and applied to a $100 \times 2.6$ cm "SEPHADEX G-50" column equilibrated with an eluent of 20 mM Tris Cl, pH 7.4, 0.15 M NaCl at a flow rate of 30 ml/h. Three major fractions were obtained following gel filtration (FIG. 2.). Suppressor activity was found in fraction B. This fraction was then lyophilized, redissolved in 10 ml water and desalted by dialysis for 24 hours against water. The sample was then lyophilized and redissolved in water to 1/5 the original volume. The fraction was then applied to a $4.5 \times 250$ mm reverse phase C-18 Alltech Vydac column (300 Å porosity), using a 0.60% isopropanol (containing 0.1 TFA) linear gradient (containing 0.1% TFA) at a flow rate of 1 ml/m for 30 minutes. Effluent was monitored at 280 nm, 2.0 AUFS. Activity was found in the peak that eluted at 2.9 m (FIG. 3), prior to starting the isopropanol gradient. Material in the 2.9 m peak was again lyophilized and redissolved in water to 1/5 the original volume. The material was then separated by gel filtration through a $270 \times 12$ mm Waters I60 Protein Pak equilibrated in water with 0.1% TFA and run at a flow rate of 0.5 ml/m for 30 minutes. Effluent was monitored at 280 nm 2.0 AUFS. Three peaks eluted at 15.3, 16.6 and 19.6 m (FIG. 4). Maximal suppressor activity was found in the 19.6 m peak. The increase in specific activity, yields and fold purification following each purification step is shown in Table 1 hereinbelow.

TABLE 1

| Purification Step | Specific Activity (u/μg)* | Yield from 200 g Wet Weight of Left Ventricle | Fold Purification |
|---|---|---|---|
| Activity and Yield After Purification Steps | | | |
| Crude Supernatant | 1.28 ± 0.12 (5)+ | 8 g | 1.0 |
| Supernatant After Heating | 10.45 ± 1.12 (5) | 964 mg | 8.16 |
| Retentate After YM Ultrafiltration | 7.32 ± 0.45 (5) | 142 mg | 5.72 |
| G-50-B | 23.41 ± 6.53 (5) | 7 mg | 18.3 |
| Activity and Yield After Purification Steps | | | |
| Purification Step | Specific Activity (u/μg)* | Yield from 200 g Wet Weight of Left Ventricle | Fold Purification |
| C 18 (2.9 m) | 49.95 ± 2.00 (5) | 130 ug | 34.0 |
| I 60 (19.7 m) | 278 ± 1.01 (8) | 80 ug | 217.0 |

$${}^*u = 1 - \left[\frac{\text{translational activity } (+ \text{ extract})}{\text{translational activity } (+ \text{ water})}\right]$$

+number of determinations

EXAMPLE 3: SDS Polyacrylamide Gel Electrophoresis

Following lyophilization of the purified protein in the 19.6 m peak, ½ of the sample was dissolved in Laemmli sample buffer and gels were run by the procedure of U.

Figure 5:
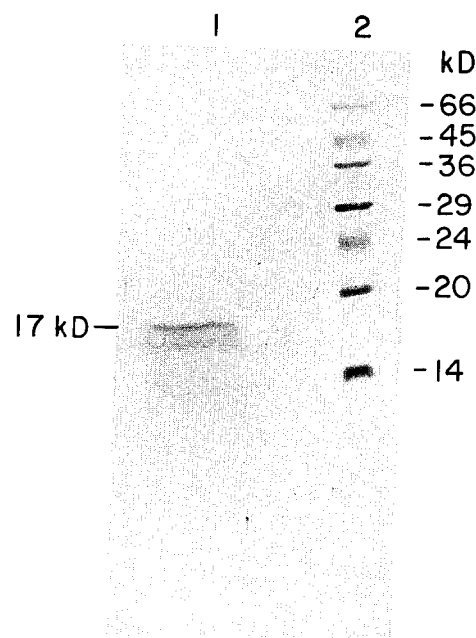
FIG. 5 is a photograph of the results of a gel electrophoresis of the translation inhibiting peptide of the present invention.

K. Laemmli, "Cleavage of Structural Proteins During the Assembly of the Head of Bacteriophage T4", *Nature*, 227, 680–685, (1987), using 15% acrylamide in the resolving gel and 5% in the stacking gel (see FIG. 5). Lane 1 of FIG. 5: 10 μg of TIP; Lane 2 of FIG. 5: Sigma molecular weight markers: Serum albumin, 66 kD; ovalbumin, 45 kD; glyceraldehyde-3-P-dehydrogenase, 36 kD; carbonic anhydrase, 29 kD; trypsinogen 24 kD; trypsin inhibitor, 20.1 kD; and lactalbumin, 14.2 kD, were run beside TIP. Gels were run one hour at 15 mamps, and two hours at 20 mamps, then stained in Coomassie Brilliant Blue R. Thereafter the gels were destained and photographed.

EXAMPLE 4: Amino Acid Analysis and Sequencing

The remainder of the sample not subjected to gel electrophoresis was used for amino acid analysis and sequencing (Table 2).

Amino acid analysis was performed on the 19.6 m peak following gel filtration by HPLC with an I60 Protein Pak (Waters); material in the peak was derivatized with phenylisothiocyanate according to the method of R. L. Heinrikson and S. C. Meredith, "Amino Acid Analysis by Reverse-phase High-performance Liquid Chromatograph Precolumn Derivatization with Phenylisothiocyanate", *Anal. Biochem.*, 136, 64–75, (1984).

Phenylthiohydantoins were identified on a Waters HPLC system. Approximately 8 Hg TIP was then sequenced out to 20 cycles on an Applied Biosystems gas phase sequencer model 470A according to the method of D. W. Speicher, G. Davis, P. D. Yurchenco and V. T. Marchesi, "Structure of Human Erythrocyte Spectrin", *J. Biol. Chem.*, 258, 14931–14937, (1983).

TABLE 2

Amino Acid Composition (A) and Partial Sequence (B) of Translational Inhibiting Peptide A. Composition

| Amino Acid | Number of residues* |
|---|---|
| Asx | 29.4 |
| Glx | 34.3 |
| Ser | 14.4 |
| Gly | 37.2 |
| His | 3.33 |
| Arg | 3.49 |
| Thr | 5.81 |
| Ala | 9.57 |
| Pro | 5.77 |
| Tyr | 2.18 |
| Val | 5.16 |
| Met | 2.25 |
| Ile | 2.66 |
| Leu | 4.96 |
| Phe | 2.11 |
| Lys | 5.54 |

B. Partial Sequence

| 1 | 2 | 3 | 4 | 5 | 6 | 7 | 8 | 9 | 10 |
|---|---|---|---|---|---|---|---|---|---|
| X | X | Thr | Ala | Ala | Ala | Lys | Phe | Glu | Arg |

| 11 | 12 | 13 | 14 | 15 | 16 | 17 | 18 | 19 | 20 |
|---|---|---|---|---|---|---|---|---|---|
| Gln | His | Met | Asp | Ser | Ser | Thr | Ser | Ala | (Ala or Asp) |

*based on 161.5 pm protein and mol. wt. for TIP of 17 kD

In the above sequence, "X" is unknown.

Figure 6:
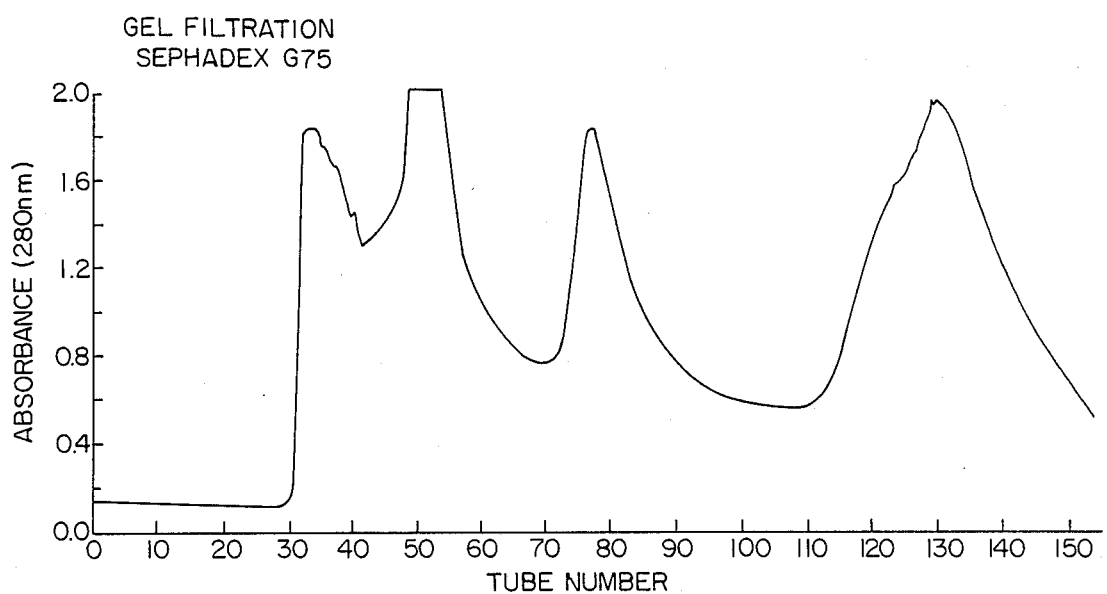
FIG. 6 is a plot showing the results of a "SEPHADEX G-75" chromatogram of unheated crude supernatant.

It was expected that a difference in TIP activities isolated from control, aortic banded and heat shocked hears would be detected. However, since such a difference was not observed, it was assumed that the 80° C. heating step may have removed or inactivated a TIP inhibitor. To test this possibility the first supernatant (unheated) from control, aortic banded and heat shocked ventricle was applied to a "SEPHADEX G-75" column (column size: 100×5.0 cm) (which provided better resolution than the G-50 column for initial separation) and the separation was run under the same conditions as described above for the "SEPHADEX G-50" column. The material separated into five major fractions (FIG. 6). Although TIP again eluted primarily in Peak B, this represents a larger particle than fraction B obtained from the "SEPHADEX G-50" column (31 Å vs. 10–15 Å), suggesting that TIP is complexed with other proteins at this more preliminary stage of purification. Fractions obtained by gel filtration on G-75 from control, aortic banded and heat shocked hearts were then assayed for their effect on translational activity (Table 3).

TABLE 3

| % Suppression ± SE (N) after G-75 Separation | | |
|---|---|---|
| Control hearts | Heat shocked | Aortic banded |
| 66.5 ± 3.3 (4) | 87.8 ± 3.7 (4) | 72.8 ± 3.8 (4) |

Control hearts vs. aortic banded P = 0.1
Control hearts vs. heat shocked P < 0.01

EXAMPLE 5: Isoelectric Point of TIP

Figure 7:
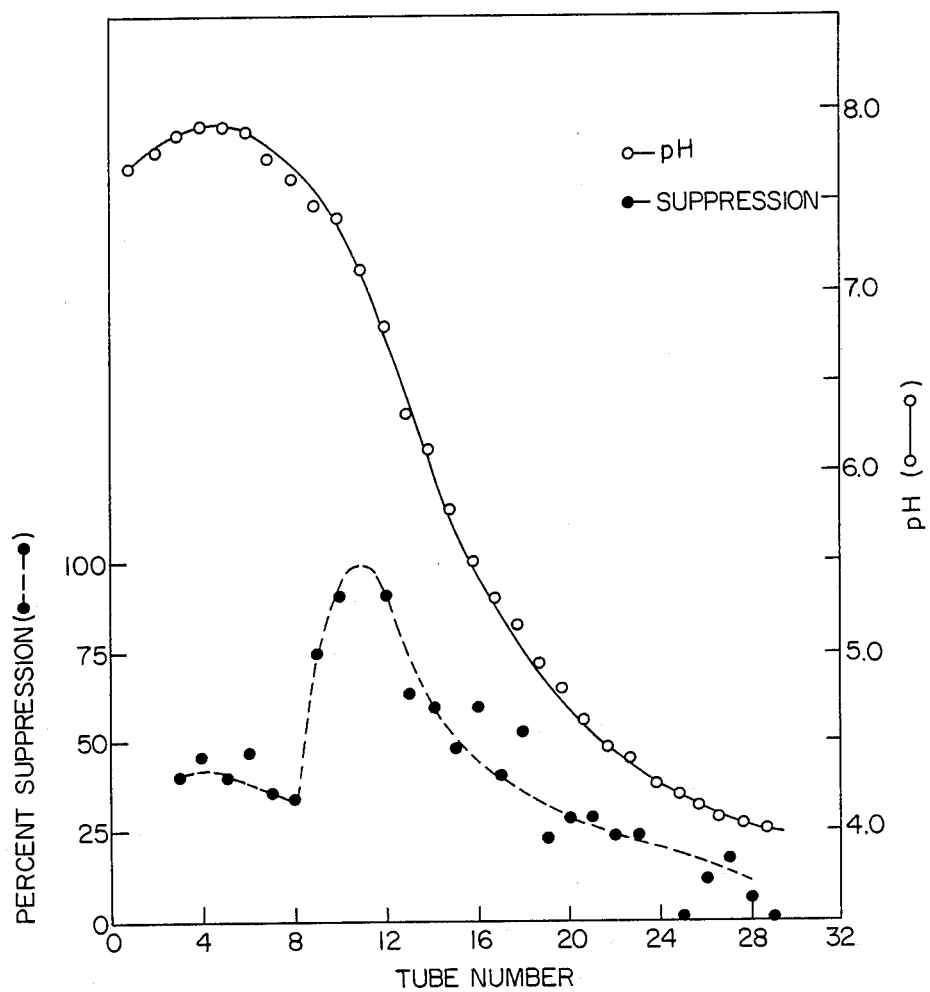
FIG. 7 is a plot depicting the results of chromatofocusing, wherein peak translational inhibiting activity is shown.

Following purification in the Waters I60 Protein Pak, approximately 3 μg of TIP was mixed with 1 mg of bovine serum albumin, to act as a carrier, and applied to a 5.0 ml chromatofocussing column (PBE 94 of Pharmacia, Uppsala, Sweden), equilibrated with 0.025 M imidazole HCl, pH 7.5. The column size was 7 mm×125 mm; flow rate: 28 ml/h. The pH gradient was developed with Polybuffer 74, adjusted to pH 4.0 at an 8-fold dilution. The pH of each fraction (4.3 ml) was read on a Beckman model 3500 digital pH meter and then assayed for translational inhibiting activity. Peak translational inhibiting activity eluted at a pH of 7.25 (FIG. 7).

EXAMPLE 6: Suppression of In Vitro Translation with TIP

Increasing amounts of TIP were added to 5.7 μg of cardiac RNA and assayed using an in vitro translation kit. All points were run in duplicate.

Figure 8:
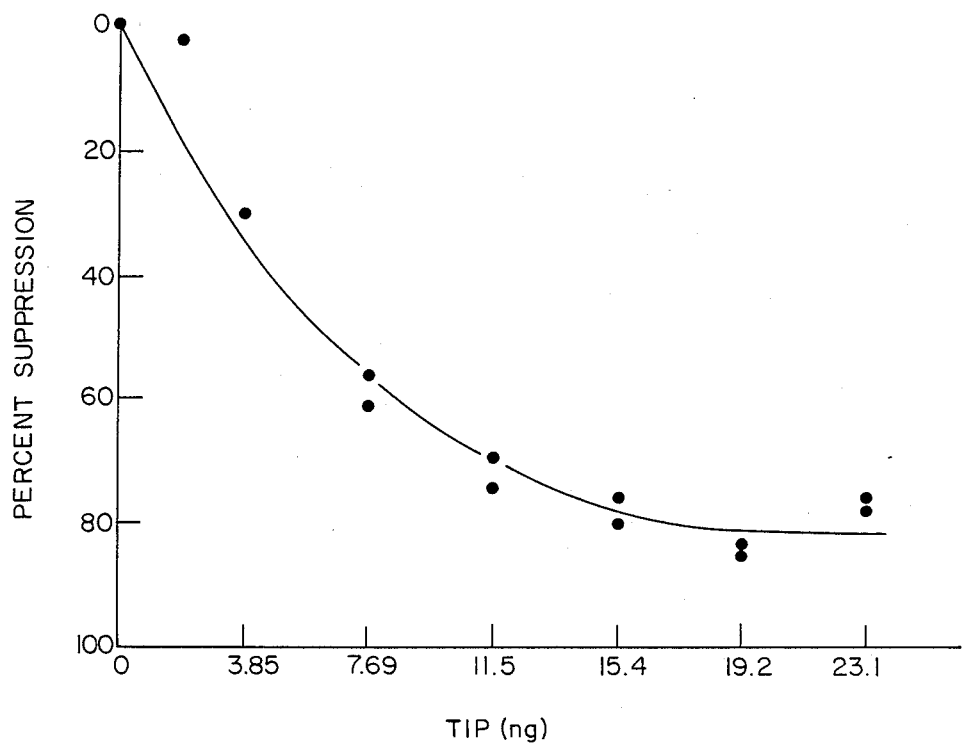
FIG. 8 is a plot showing suppression of in vitro translation with TIP.

Proteins purified as described in Example 2 hereinabove were assayed in vitro for translational activity as follows: canine cardiac RNA (5 μg) isolated from control hearts as described in G. L. Hammond, E. Wieben and C. L. Markert, "Molecular Signals for Initiating Protein Synthesis in Organ Hypertrophy", *Proc. Natl. Acad. Sci.*, 76, 2455–2459, (1979) and 3 μl of the fraction to be tested were added to 25 μl of a commercial translation mixture obtained from New England Nuclear (Boston, Mass., U.S.A) (NEN 001). In order to compare the effect of various fractions on translational activity, each assay was run simultaneously with an assay to which 3 μl of water was added in lieu of the fraction being tested. Following a 30 minute incubation at 37° C., 10 μl aliquots of the translation mixture were spotted onto 3 mm Whatman filter paper discs. The paper discs were then boiled in 10% TCA, rinsed twice with water, ethanol and acetone and air dried. Incorporation of $^{35}$S-methionine into newly translated protein was quantited by counting in 10 ml of Liquiscint (National Diagnostics, Somerville, N.J., U.S.A.). Percent suppression was determined as described for Table 1, using translation in the absence of TIP as a control for 0% suppression. Suppression in the synthesis of normal cardiac RNA plateaued at 80% (FIG. 8). However, the effect on stress related RNA's such as SP70 mRNA is unknown and may be different—the difference could be quantitated with TIP.

When 3.27 ng of TIP was added to the in vitro translation assay containing 5.7 μg of cardiac RNA, a 24% suppression in translation was observed (FIG. 8). Therefore, using the linear portion of the suppression curve, 2.4 ng of TIP would completely inhibit the translation of 1 μg of RNA.

EXAMPLE 7: Polysome Sedimentation

Figure 9:
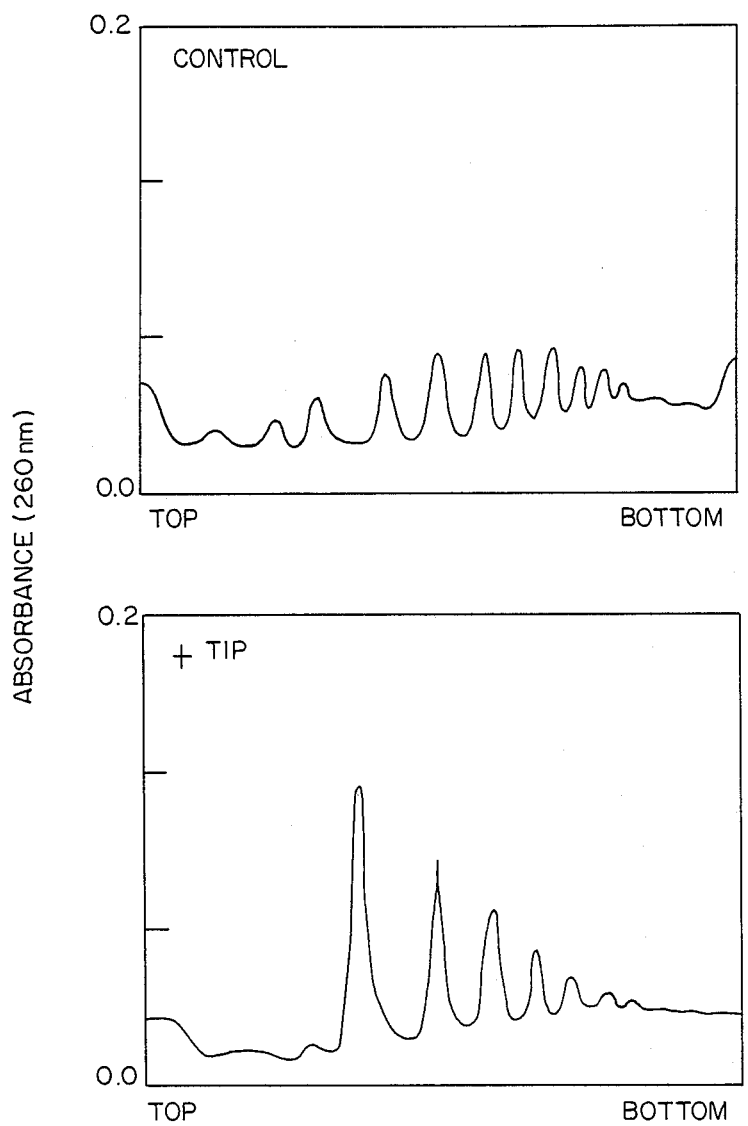
FIG. 9 shows two plots depicting sedimentation distribution of cardiac polysomes isolated from control tissue incubated with TIP.

Polysomes were isolated from control canine ventricle by a modification of the method of Lai, Harve and Hammond, *Biochem. Biophys. Res. Comm.*, 134, 166–171, (1986). Step gradients were formed using 4 ml of 2.0 M sucrose, 1 ml of 1.5 M sucrose and 7 ml of sample. Following a 16 hour centrifugation at 4° C. at 270,000×g, the polysome pellet was washed with 100 μl of gradient buffer and resuspended in the same buffer. The suspended polysomes were centrifuged briefly (one minute) in an Eppendorf centrifuge and the supernatant diluted with gradient buffer so that 10 $A_{260}$ units/ml were obtained. Approximately 45 ng of TIP and 200 μl of water were added and following an 80 minute incubation period, the samples were layered on 12 ml sucrose gradients consisting of 0.4–1.2 M sucrose and centrifuged at 270,000×g for 100 minutes at 4° C.. Controls were run in the same manner, except that water only was added to the polysomes. The treated polysomes were centrifuged for 100 m on 0.4–1.2 M sucrose gradients. The gradients were fractionated by pumping sucrose from the bottom of the tube and the absorbance was monitored at 260 nm. The resulting sedimentation distribution profiles were obtained with an ISCO gradient fractionator and an UV monitor (FIG. 9).

The shift in the sedimentation distribution of polysomes obtained from control cardiac tissue treated with TIP strongly resembles the sedimentation profile obtained from a heat stressed heart (Lai, Havre and Hammond, *Biochem. Biophys. Res. Comm.*, 13., 166–171, (1986)).

It will be appreciated that the instant specification and claims are set forth by way of illustration and not limitation and that various modifications and changes may be made without departing from the spirit and scope of the present invention.

What is claimed is:

1. A purified that causes a suppression in protein synthesis by halting the translation of mRNA into protein, said peptide having a molecular weight, determined by SDS-PAGE, of 12 to 17 kD, having an isoelectric point of 7 to 7.25, having a Stokes radius of less than 16 Angstroms and having a partial amino acid sequence for positions 3 to 20 as follows: Thr-Ala-Ala-Ala-Lys-Phe-Glu-Arg-Gln-His-Met-Asp-Ser-Ser-Thr-Ser-Ala-(Ala or Asp).

2. A peptide according to claim 1, wherein the molecular weight is 17 kD.

3. A peptide according to claim 1, wherein the isoelectric point is 7.25.

4. A peptide according to claim 3, wherein the peptide has a Stokes radius of 10 to 15 Angstoms.

5. A peptide according to claim 1, wherein said peptide is isolated from cardiac tissue.

6. A peptide according to claim 5, wherein the cardiac tissue is canine cardiac tissue.

7. A peptide according to claim 1, wherein said peptide is water soluble.

8. A peptide according to claim 1, produced by
  (a) homogenizing tissue from a ventricle of an animal,
  (b) centrifuging the homogenized tissue from step (a),
  (c) heating the centrifuged tissue from step (b) at 80° to 85° C. to form a supernatant,
  (d) subjecting the supernatant from step (c) to ultrafiltration to form an ultrafiltrate and a retentate,
  (e) lyophilizing the retentate from step (d),
  (f) dialyzing the product from step (e),
  (g) subjecting the product of step (f) to high pressure liquid chromatography to form fractions,
  (h) lypophilizing a fraction from step (g) and
  (i) subjecting the product from step (h) to high pressure liquid chromatography.

9. A peptide according to claim 1, having a specific activity of 278±1.01 u/μg in inhibiting translation.

10. A method of treating a polysome preparation obtained from cardiac tissue and having a particular polysome distribution, comprising contacting said preparation with a peptide according to claim 1, whereby there results a shift in the polysome distribution to a distribution in which monosomes are the predominate form.

11. A peptide according to claim 1 having the composition as set forth in Table 2 in the specification.

* * * * *